(12) United States Patent
Bradley

(10) Patent No.: US 7,162,304 B1
(45) Date of Patent: Jan. 9, 2007

(54) SYSTEM FOR MEASURING CARDIAC RHYTHM PARAMETERS FOR ASSESSMENT OF SPINAL CORD STIMULATION

(75) Inventor: Kerry Bradley, Glendale, CA (US)

(73) Assignee: Advanced Bionics Corporation, Valencia, CA (US)

( * ) Notice: Subject to any disclaimer, the term of this patent is extended or adjusted under 35 U.S.C. 154(b) by 85 days.

(21) Appl. No.: 10/839,476

(22) Filed: May 5, 2004

Related U.S. Application Data

(60) Provisional application No. 60/469,084, filed on May 8, 2003.

(51) Int. Cl.
*A61N 1/34* (2006.01)
*A61B 5/04* (2006.01)

(52) U.S. Cl. .................. 607/46; 607/117; 600/509

(58) Field of Classification Search ............. 607/46, 607/117; 600/509
See application file for complete search history.

(56) References Cited

U.S. PATENT DOCUMENTS

| | | | |
|---|---|---|---|
| 3,646,940 A | 3/1972 | Timm et al. | |
| 3,662,759 A * | 5/1972 | Dabolt | 607/9 |
| 3,724,467 A | 4/1973 | Avery et al. | |
| 3,903,897 A * | 9/1975 | Woollons et al. | 607/9 |
| 4,331,157 A * | 5/1982 | Keller et al. | 600/509 |
| 5,458,626 A * | 10/1995 | Krause | 607/50 |
| 5,782,882 A * | 7/1998 | Lerman et al. | 607/10 |
| 5,824,033 A * | 10/1998 | Ferrari | 607/142 |
| 6,516,227 B1 * | 2/2003 | Meadows et al. | 607/46 |
| 6,711,442 B1 * | 3/2004 | Swerdlow et al. | 607/63 |
| 6,731,986 B1 * | 5/2004 | Mann | 607/30 |

* cited by examiner

*Primary Examiner*—Mark Bockelman
(74) *Attorney, Agent, or Firm*—Bryant R. Gold; Philip H. Lee; Travis K. Laird

(57) ABSTRACT

A neuro-stimulation system and method are provided which can monitor EKG signals and provide electrical stimulation. The system comprises a stimulation lead having at least one stimulating electrode on the lead and an IPG having a case and connectors. The connectors can mechanically and electrical connect to the lead and to the at least one stimulating electrode and an EKG electrode can be placed on the stimulating lead. The IPG case may be used variously as an EKG electrode, as well as an indifferent electrode. Alternatively or additionally, a separate, second lead having a second EKG electrode may be connected to the IPG. This second EKG electrode may also double in function as a stimulation electrode.

10 Claims, 7 Drawing Sheets

SYSTEM FOR MEASURING CARDIAC RHYTHM PARAMETERS FOR ASSESSMENT OF SPINAL CORD STIMULATION

The present application claims the benefit of U.S. Provisional Patent Application Ser. No. 60/469,084, filed May 8, 2003, which application is herein incorporated by reference in its entirety.

BACKGROUND OF THE INVENTION

The present invention relates to electrical stimulation for treating chronic pain and, more particularly, systems and methods for delivering stimulation that can also monitor cardiac function.

The present invention may be used with spinal cord stimulation therapies in which a neurostimulator is used to stimulate dorsal column nerves. Spinal cord stimulation (SCS) systems treat chronic pain by providing electrical stimulation pulses through the electrodes of an electrode array placed epidurally near a patient's spine. SCS is a well-accepted clinical method for reducing pain in certain populations of patients. SCS systems typically include an Implantable Pulse Generator (IPG) coupled to an array of electrodes at or near the distal end of an electrode lead. The IPG generates electrical pulses that are delivered to neural tissue, e.g., nerve fibers within the spinal cord, through the electrodes of the electrode array.

In one type of SCS system, the electrodes are implanted proximal to the dura mater of the spinal cord. Individual electrode contacts (the "electrodes") may be arranged in a desired pattern and spacing in order to create an electrode array. Individual conductor wires can connect with each electrode in the array. The electrode leads exit the spinal cord and attach to the IPG, either directly or through one or more electrode lead extensions. The electrode lead extension, in turn, is typically tunneled around the torso of the patient to a subcutaneous pocket where the IPG is implanted.

The electrical pulses generated by the SCS stimulation system, or other neural system, are also referred to as "stimulation pulses". In an SCS system, the stimulation pulses typically have the effect of producing a tingling sensation, also known as a paresthesia. The amplitude of the stimulation pulses affects the intensity of the paresthesia felt by the patient. In general, it is desirable to have the amplitude of stimulation comfortably set to a level which produces paresthesia to block pain but not above a level that may actually result in pain apart from the native pain. Moreover, the stimulus amplitude should be set to a stimulus level lower than that which can recruit reflex motor nerves that can cause involuntary muscle contractions.

SCS and other stimulation systems are known in the art. For example, an implantable electronic stimulator is disclosed in U.S. Pat. No. 3,646,940 that provides timed, sequenced electrical impulses to a plurality of electrodes. As another example, U.S. Pat. No. 3,724,467 teaches an electrode implant for neuro-stimulation of the spinal cord.

In addition to pain caused by injury to the nerve in the spinal area, chronic pain may also be caused by neuropathic conditions. Such neuropathic conditions include those caused by anginal pain and those caused by peripheral vascular diseases. Neuropathic pain can often be successfully relieved by applying electrical stimulation to the affected area of the body, either via peripheral nerve or spinal cord stimulation.

Chronic pain patients often have reduced exercise capacity as well as limited physical movement. In many cases, it is the chronic pain condition which prevents the patient from having an active life or from pursuing any forms of exercise. One goal of therapy for those suffering from chronic pain is to encourage patients to increase their physical activity. However, up to now, with exception of verbal feedback recounting a patient's own activity, there has been no reliable method to monitor patient activity or inactivity.

Accordingly, what is needed is a system for measuring cardiac rhythm parameters in patients as an adjunct to SCS and other stimulation treatments for chronic pain.

SUMMARY OF THE INVENTION

The present invention addresses the above and other needs by providing a system and method for delivering spinal cord stimulation therapy and also a means for monitoring patient activity employing electrocardiograms ("EKG").

In accordance with one aspect of the invention, an implantable stimulator system is provided that comprises an electro-cardiogram ("EKG") monitoring system that is built into the implantable stimulator and lead system.

In one embodiment of the invention, the system can comprise: a first stimulation lead having at least one stimulating electrode on the lead; an IPG having a case and connector, which connector can mechanically and electrically connect to the first stimulation lead; and a first EKG electrode on the first stimulation lead. This EKG electrode is preferably placed substantially distal on the first stimulation lead.

In another embodiment of the invention, the system can comprise: a first stimulation lead having at least one stimulating electrode on the lead for stimulating nerves in a human spinal cord; and an IPG having a case and connector, which connector can mechanically and electrical connect to the lead, wherein the at least one stimulating electrode also functions as an EKG electrode when it is not operating as a stimulating electrode.

In other embodiments of the system, a second lead that is connected to the IPG may have a second EKG, which is preferably placed substantially distal on the second lead. The stimulation mode may be a bipolar mode, where the IPG case functions as an EKG electrode. Alternatively, the stimulation mode may be a monopolar, where the case functions as an indifferent, return electrode, during delivery of stimulation current to target nerves. The IPG case may also function as an EKG electrode in a time-multiplexed fashion, i.e., when not operating as an indifferent electrode as part of the monopolar stimulation circuit.

The IPG case may also be used as an EKG electrode. Alternatively or additionally, a separate, second lead having a second EKG electrode may be connected to the IPG. Thus, at least two EKG electrodes are provided in order to obtain EKG recordings.

In accordance with another aspect of the invention, a method is provided for monitoring cardiac activity in chronically stimulated patients, which method records EKG signals over time as a function of the stimulation applied.

One embodiment of the method comprises: implanting an IPG having a stimulating lead connected, which lead has at least one stimulating electrode and one EKG electrode attached; periodically stimulating the patient's spinal cord with the stimulating electrode; periodically monitoring and recording EKG data using the EKG electrode; storing the recorded EKG data in IPG memory; and downloading the EKG data to an external, non-implanted device, e.g., a programmer.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 2:
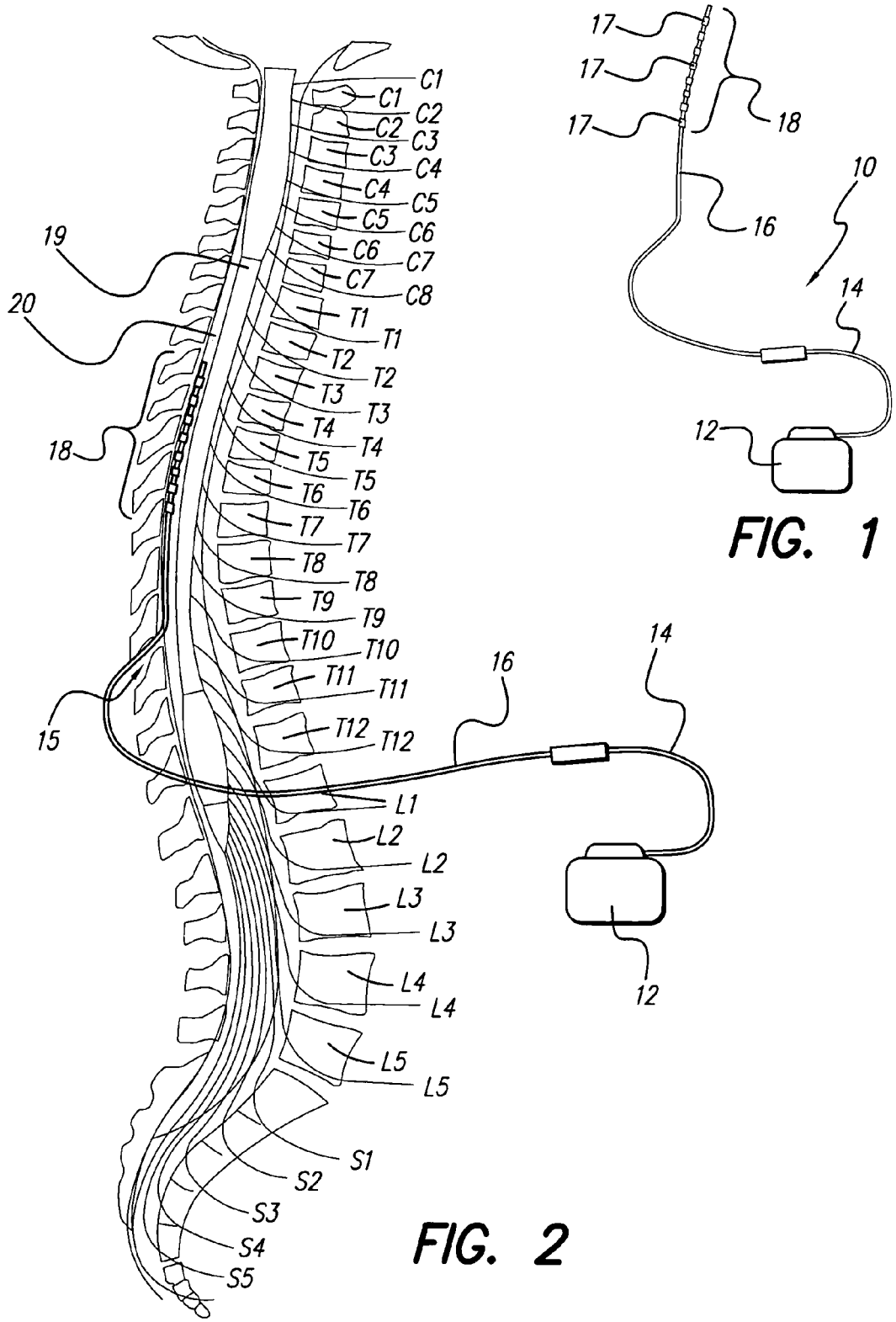
FIG. 1 shows a generalized spinal cord stimulation system.
FIG. 2 shows a side, cross-sectional view of a human spinal cord with an electrode array implanted.

FIG. 1 shows a representative neural stimulation system 10. Such a system typically comprises an implantable pulse generator (IPG) 12, a lead extension 14, an electrode lead 16, and an electrode array 18. The electrode array includes a plurality of electrode contacts 17 (also referred to as "electrodes"). The electrodes 17 are arranged, for example, in an in-line array 18 near the distal end of the lead 16. Other electrode array configurations may also be used. The IPG 12 generates stimulation current pulses that are applied to selected electrodes 17 within the electrode array 18.

A proximal end of the lead extension 14 can be removably connected to the IPG 12, and a distal end of the lead extension 14 can be removably connected to a proximal end of the electrode lead 16. The electrode array 18 is formed on a distal end of the electrode lead 16. The in-series combination of the lead extension 14 and electrode lead 16 carry the stimulation current from the IPG 12 to electrodes 17 of the electrode array 18. It should be noted that the lead extension 14 need not always be used with the neural stimulation system 10 but may be used when the physical distance between the IPG 12 and the electrode array 18 requires its use.

FIG. 2 shows a side, cross-sectional view of a spinal cord with electrode array 18 implanted for spinal cord stimulation (SCS). The lead 16 and, more particularly, the electrode array 18 are implanted in the epidural space 20 of a patient in close proximity to the spinal cord 19. Due to the lack of space near the lead exit point 15 where the electrode lead 16 exits the spinal column, the IPG 12 is generally implanted in the abdomen or above the buttocks. The lead extension 14 facilitates locating the IPG 12 away from the lead exit point 15.

A more complete description of an SCS system may be found in U.S. Pat. No. 6,516,227 and is incorporated herein by reference in its entirety.

Figure 3:
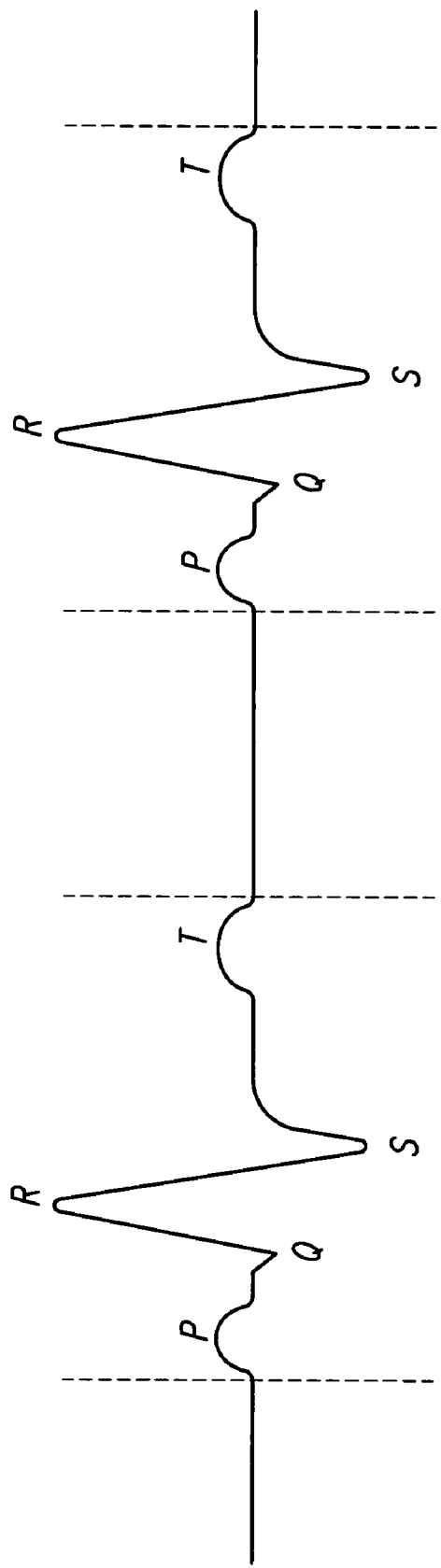
FIG. 3 shows a data sample of an electrocardiogram (EKG) showing electrical activity of two cardiac cycles.

FIG. 3 shows a diagrammatic representation of an EKG. A complete cardiac cycle includes a P wave, a QRS complex and a T wave. The P wave represents atrial depolarization. Depolarization occurs when both atria are conducting electrical signals and both atria are contracting. The QRS complex represents ventricular depolarization when both heart ventricles are contracting. There is a plateau phase between the S wave and the beginning of the T wave, which represents a portion of the ventricular repolarization. The T wave represents the rapid phase of ventricular repolarization. The heart rate is calculated by taking one point on a cardiac cycle and measuring the time, $T_H$, until the occurrence of the same point of the next cardiac cycle, e.g., the time between the peak of the R wave to the peak of the next R wave. The reciprocal of this time, $T_H$, between the two R waves is $1/T_H$ and this reciprocal value is the heart rate.

Figure 4:
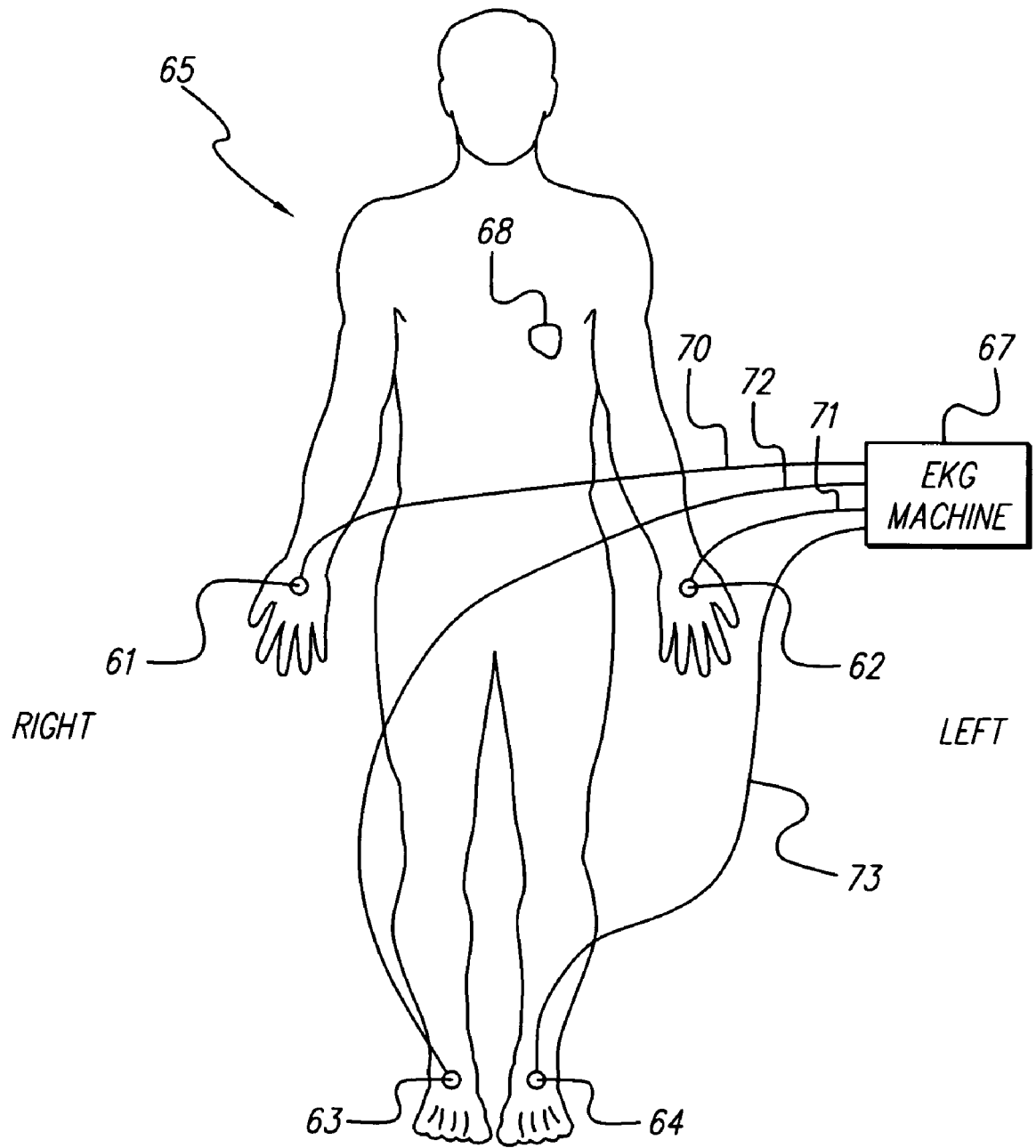
FIG. 4 shows a representation of electrode placement on a patient for obtaining surface EKG signals.

FIG. 4 shows a representation of a patient 65 and EKG lead connections that may be used to obtain EKG signals. Four EKG electrodes 61, 62, 63 and 64 are shown on the patient's limbs and each EKG electrode is connected by leads 70, 71, 72 and 73, respectively. The leads are connected to an EKG machine 67 that can produce a visual display or an EKG paper strip.

Figure 5:
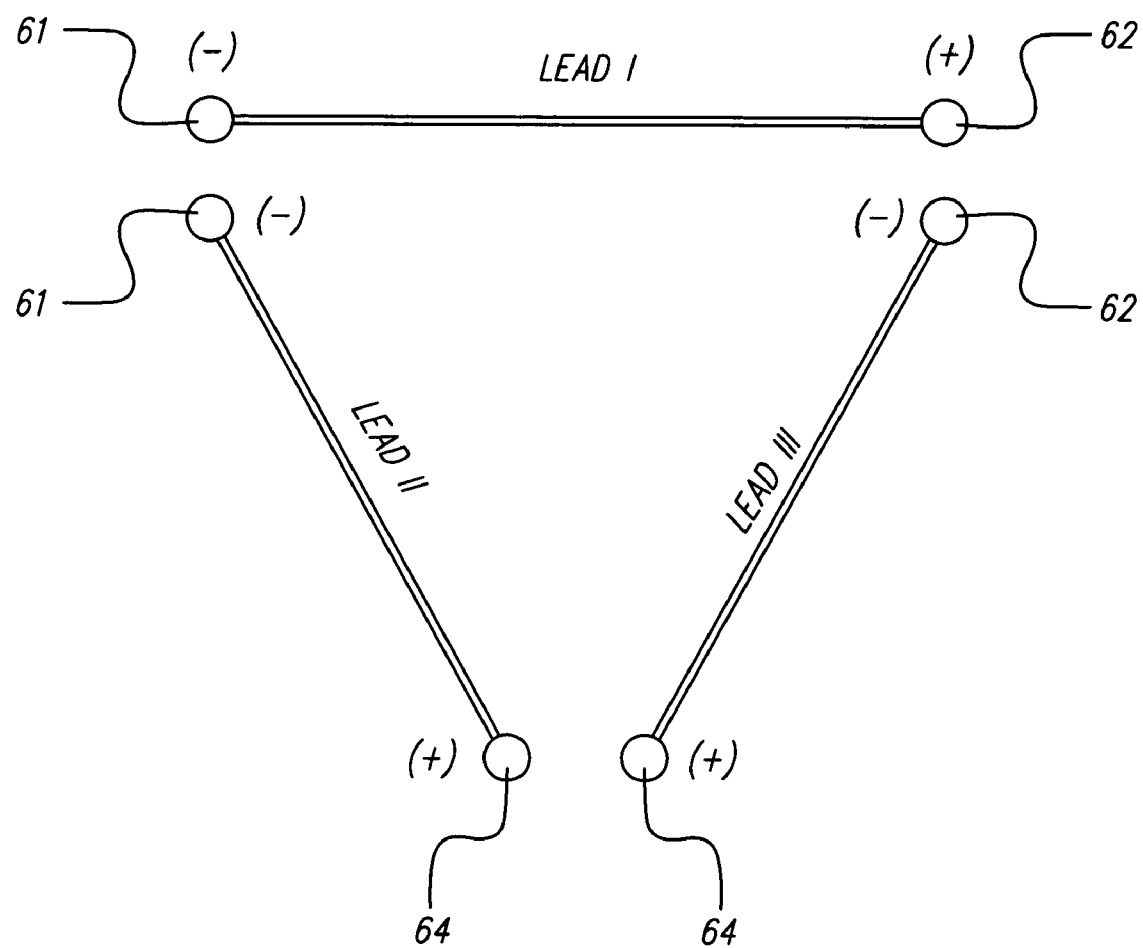
FIG. 5 shows representations of Lead I, Lead II and Lead III vectors.

FIG. 5 shows a diagrammatic representation of EKG lead configurations, Lead I, Lead II and Lead III. Here, the use of the terms "Lead I, Lead II and Lead III" refers not to a physical lead that carries an electrode but is, instead, a specific designation for bipolar electrode placements on a person for measuring EKG signals. As shown in FIG. 5, the Lead I Vector is represented by electrodes 61(−) and 62(+); the Lead II Vector is represented by electrodes 61(−) and 62(+); and the Lead III Vector is represented by electrodes 62 (−) and 64(+). Note that electrode 62 may be either negative or positive depending on the particular lead vector being measured.

Another common EKG electrode configuration uses electrode 64 as a positive connection and both electrodes 61 and 62 as negative connections. This type of EKG lead configuration is a combination of Lead II and Lead III Vectors and is called an AVF lead configuration. (For a more detailed discussion of Lead I, II and III Vector configurations, see Dale Dubin, Rapid Interpretation of EKG's, Cover Publishing Company, 1996, 5th edition).

The minimum number of EKG electrodes that must be used to sense cardiac electrical activity is two. In many cases, three EKG electrodes are used to obtain good EKG readings. When only two EKG electrodes are used, EKG electrodes 61 and 62 may be chosen, placing the heart 68 physically in the middle of the two electrodes. Alternatively, electrodes 61 and 64 may be selected, instead, so that the bipolar measurement vector is better aligned with the sequential atrial-to-ventricular depolarization vector.

Figure 6:
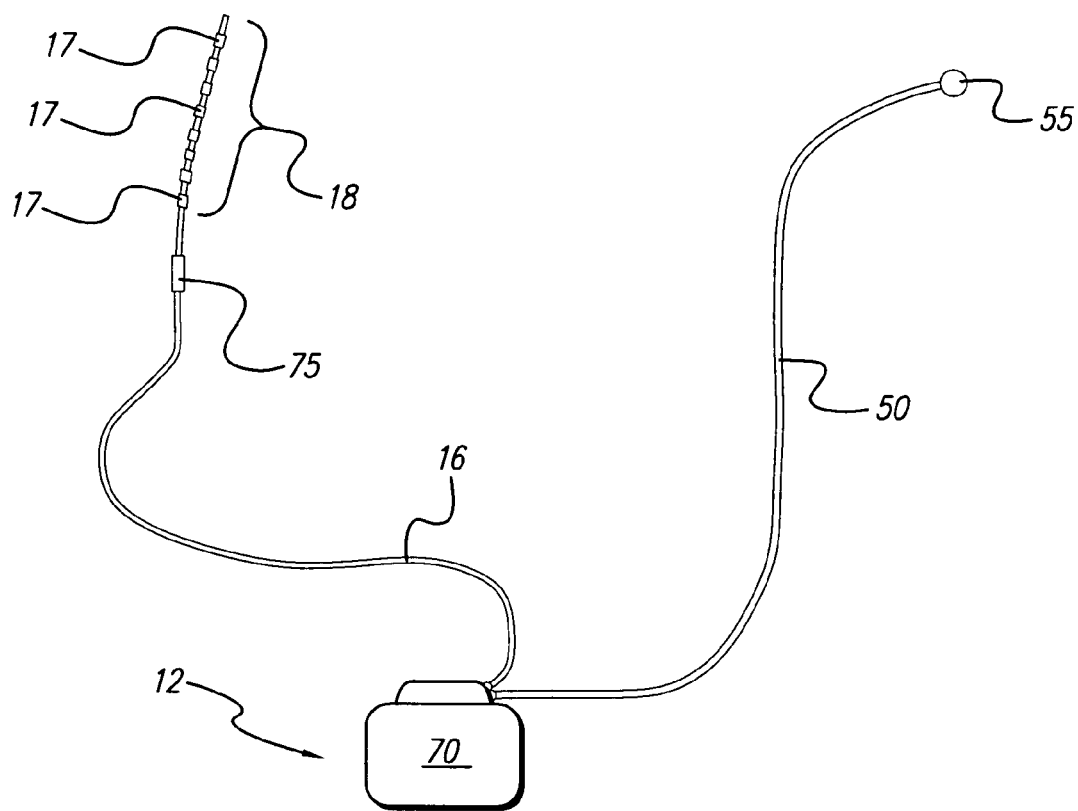
FIG. 6 shows, in accordance with the present invention, an embodiment of a stimulation system having cardiac monitoring capability.

FIG. 6 shows, in accordance with the present invention, an embodiment of the neurostimulator system for use in spinal cord stimulation that includes a system for measuring cardiac rhythm parameters. As in the conventional stimulator system, this system includes an IPG 12, a lead 16 having an electrode array 18 with a plurality of electrodes 17 at or near its distal end. However, in the present invention, the lead 16 may also include a first EKG electrode 75. This first EKG electrode 75 is connected by a separate conductor wire in lead 16 and EKG electrode 75 is not electrically connected to any of the stimulation electrodes 17 during delivery of stimulation current. In some embodiments, however, lead 16 may not have a dedicated EKG electrode 75 but may, instead, have only one or more stimulating electrode(s) 17, which one or more electrodes may also double in function as an EKG electrode.

In addition, in one embodiment, the stimulator system may include a second lead 50 connected to IPG 12, which second lead can have, at or near the distal end, a second EKG electrode 55 which is used as part of the EKG monitoring system. Also, second lead 50 may function, in some cases, as another neurostimulation lead for stimulating another region of the patient's body, either peripherally or centrally, e.g., at the brain or the spinal cord.

The IPG case 70 may function solely as an indifferent electrode, no electrode or, in some instances, as another EKG electrode. The case 70 also may function as each of the three modes, at various time periods, simply by switching modes. It should be noted that the IPG case 70 typically does not function as an EKG electrode during the time that the case functions as a return, indifferent electrode, thereby completing an electrical circuit with any stimulating electrode on the first lead 16 or on second lead 50.

Any of the electrodes 17 may also be used as an EKG sensing electrode. Although it is preferred to use dedicated EKG electrodes that are not involved in stimulation, it is possible to use one or more of the stimulation electrodes 17 as EKG electrodes, provided such stimulation electrodes are not simultaneously operating as stimulation electrodes and passing current. The electrodes 17 may be ganged together during EKG sensing in order to increase the effective electrode surface area. Additionally, other electrodes (not shown) on lead 50 may also function dually as stimulation electrodes and EKG electrodes, employing switching circuitry in the IPG 12.

Figure 7A:
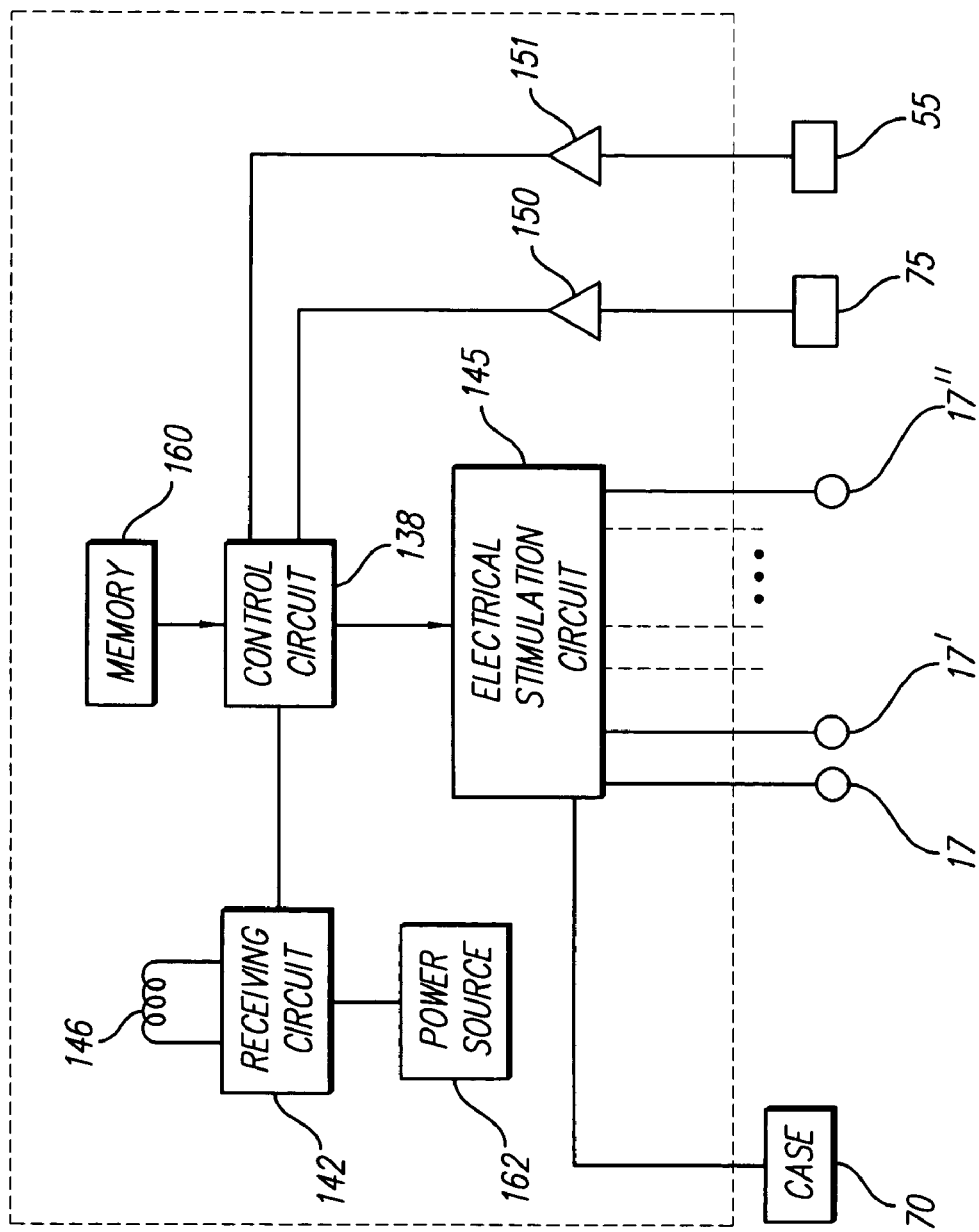
FIGS. 7A and 7B show, in accordance with the present invention, embodiments of functional block diagrams of circuitries for implementing electrical stimulation and also monitoring cardiac rhythms by measuring EKG signals.
Figure 7B:
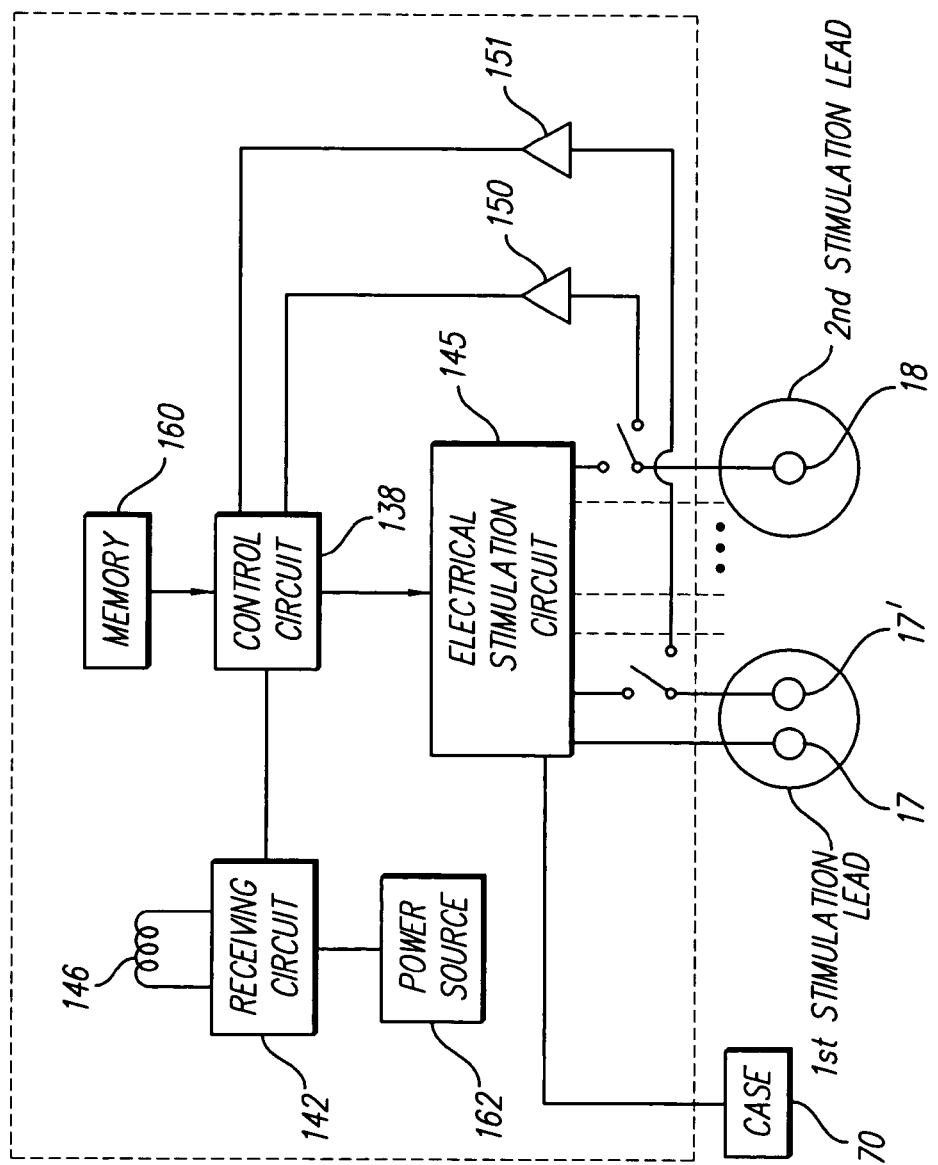

FIGS. 7A and 7B show exemplary embodiments of the internal circuitry that may be contained in the IPG 12. The dashed line enclosing the internal circuitry represents the boundary of a hermetically-sealed case containing a system control circuit (SCU) 138, a power/data receiving circuit 142, electrical stimulation circuit 145, for example, a pulse or current generator circuitry. The stimulation circuit 145 may be connected to at least two electrodes, represented here as 17, 17' and 17". The SCU 138 may be connected to a programmable memory 160 and a power source/storage 162. In addition, an inductive coil 146 may be included for receiving and transmitting RF data or energy between inductive coil 146 and an external coil (not shown). An IPG case 70 may be selectively connected in a circuit with one of the electrodes 17, 17' and 17". Or the case 70 may be selectively connected to an EKG circuit. The dashed lines coming from the electrical stimulation circuit 145 and the three heavy dots indicate that additional electrical connections may be made with additional electrodes which are not shown. All of these electrodes may be placed physically on a first stimulation lead or placed on additional leads, such as a second or a third stimulation lead. All of the leads may be connected to the electrical stimulation circuit 145.

FIG. 7A shows EKG electrode 75 which may be placed, for example, on lead 16, as shown in FIG. 6, or on a separate, dedicated lead having only the EKG electrode 75. EKG electrode 55 may be placed on a second, dedicated lead, as shown in FIG. 6, or electrode 55 may be placed together with other stimulation leads (not shown). Each EKG electrode 75 and 55, however, must be connected to a sense amplifiers 150 and 151, respectively, in order to sense EKG information, which information can be sent to the control unit 138 for processing. The processed EKG data can then be sent to programmable memory 160 for short-term or long-term storage. Programmable memory 160 may be used to store set(s) of data, stimulation and control parameters and other data, in addition to EKG data.

FIG. 7B shows an alternative embodiment of the circuitry contained in the IPG 70, in accordance with the present invention. In this embodiment there are no separate EKG electrodes used. Instead, stimulation electrodes 17, 17' and 18 may double in function as EKG electrodes. Electrodes 17 and 17' are physically located on a first stimulation lead and electrode 18 is located on a second stimulation lead. The depiction of only one or two stimulation electrodes per lead, as shown in FIG. 7B, is not intended to be limiting, as there may be more than two electrodes per lead.

The implanted IPG 12 of FIG. 6, having a circuitry as shown in FIGS. 7A and 7B, may include the following powering options: (1) an external power source coupled to the IPG via radio-frequency (RF) link (2) a self-contained power source 162 via any means of generation or storage of energy, e.g., a primary battery, a rechargeable battery, or a capacitor; and (3) if the self-contained power source is rechargeable, a means of recharging the power source, e.g., an RF link.

Table 1 illustrates, in accordance with the invention, some possible EKG modes of the present system, where an "X" indicates that an electrode functions as an EKG electrode.

TABLE 1

Modes of EKG and stimulation connections.

| Stimulation Mode and EKG Mode | Electrode 17 | IPG case 70 | EKG electrode 55 | EKG electrode 75 |
|---|---|---|---|---|
| Monopolar Stimulation/ Two Lead EKG | One electrode 17 | X - functions as EKG electrode when stimulation pulses are off, and is an indifferent electrode at other times. | not connected or absent | X |
| Monopolar Stimulation/ Two Lead EKG | One electrode 17 | functions as indifferent electrode | X | X |
| Bipolar Stimulation/Two Lead EKG | Two electrodes among 17, 17' and 17" | X - functions as EKG electrode | X | not connected or absent |
| Bipolar Stimula- | Two electrodes among | not connected | X | X |

TABLE 1-continued

Modes of EKG and stimulation connections.

| Stimulation Mode and EKG Mode | Electrode 17 | IPG case 70 | EKG electrode 55 | EKG electrode 75 |
|---|---|---|---|---|
| tion/Two Lead EKG | 17, 17', and 17''' | | | |
| Bipolar Stimulation/Two Lead EKG | Two electrodes among 17, 17', and 17''' | X - functions as EKG electrode | not connected or absent | X |
| Bipolar Stimulation/Three lead EKG | Two electrodes among 17, 17'', and 17''' | X - functions as EKG electrode | X | X |
| Monopolar Stimulation/Two lead EKG | One electrode 17 functions as an EKG electrode and at different times, a stimulating electrode | not connected | X | Not connected |

Note "X" means connected as EKG electrode.

In general there must be at least two EKG electrodes spaced a distance apart within the body to obtain a usable EKG recording. The configurations listed in Table 1 are not an exhaustive list of the possible combinations and, moreover, they do not include the possibility of a stimulating electrode on second lead 50, which may double as an EKG electrode.

The EKG may be measured on any two or more of the EKG functioning electrodes (as shown in Table 1), preferably in an electrode configuration mode which yields a lead II or lead III (rostro-caudal) vector. At least two EKG electrodes may be variously connected using programmable switches to connect the EKG electrodes (or any stimulating electrodes functioning as EKG electrodes) to sense amplifier 150 or 151 in IPG 12 wherein the EKG of the patient may be sampled for specific programmed time periods, e.g., intermittently at one minute sampling durations over a period of several days, several weeks or months. In some examples, the EKG is sensed during times when stimulation is not being delivered in order to avoid sensing the field potentials established by the volume conductor of the body.

If sensing is performed concurrently to the delivery of stimulation, the R waves may be obscured by stimulation pulse artifacts. It may be necessary to employ processing methods to reacquire or extrapolate the R waves through long-term data acquisition and/or averaging of R to R intervals. The sampled EKG waveforms and heart rates can be stored in memory within the IPG and down-loaded to an external programmer using an RF or other communication link. The EKG data may then be analyzed according to heart rate variability over the span of days, weeks or months. The difference in the variability of heart rate and other cardiac parameters at the start of stimulation treatment and at the time of analysis may be compared. The EKG information may also be used to analyze sympathetic and parasympathetic activity, as well as sympatho-vagal balance in patients with chronic pain.

Furthermore, the EKG may be interpreted to assess the circadian variations in heart rate, so that sleep patterns may be analyzed. An improvement or a normalization of sleep patterns is one known benefit arising from the relief or reduction of chronic pain. To assess various cardiac conditions, the EKG waveforms of individual heartbeats can be monitored, thereby providing further diagnostic patient information at the ready disposal of the clinician, who may use this information to monitor the onset or development of any abnormal, heart conditions.

The transferred EKG data from the IPG may be viewed in its raw state on a display which is attached to an IPG programmer or viewed in its processed form, e.g., charts and graphs, so that a clinician can assess the cardiovascular condition of the patient.

In some examples, the obtained EKG information can provide the clinician with the long-term variability of heart rate as a function of various stimulation parameters, which can provide a true indication of the overall activity level of the patient by eliminating patient bias and subjectivity in reporting physical activity.

While the invention herein disclosed has been described by means of specific embodiments and applications thereof, numerous modifications and variations could be made thereto by those skilled in the art without departing from the scope of the invention set forth in the claims.

What is claimed is:

1. A method of monitoring patient cardiac activity in a chronically neurostimulated patient comprising:
    implanting an IPG having a stimulating lead connected, which lead has at least one stimulating electrode and one EKG electrode attached;
    periodically stimulating the patient's spinal cord with the stimulating electrode;
    periodically monitoring and recording EKG data using the EKG electrode;
    storing the recorded EKG data in IPG memory; and
    downloading the EKG data to an external device.

2. The method of claim 1, further comprising:
    analyzing the EKG data to evaluate long-term cardiac activity of the patient, and to determine patient physical activity.

3. The method of claim 1, further comprising:
    analyzing the EKG data to evaluate the long-term cardiac activity as a function of applied stimulation.

4. The method of claim 1, further comprising:
    analyzing the EKG data to evaluate the long-term cardiac activity of the patient and to deduce sleep patterns and circadian rhythms.

5. A method of monitoring cardiac activity in a patient, said method comprising:
    providing an implantable pulse generator (IPG) having a lead coupled thereto, said lead having at least one electrode disposed thereon;

stimulating a spinal cord of said patient with said at least one electrode; and sensing electro-cardiogram (EKG) data with said at least one electrode.

6. The method of claim 5, further comprising recording said EKG data and storing said recorded EKG data in a memory unit of said IPG.

7. The method of claim 5, further comprising downloading said EKG data to an external device.

8. The method of claim 5, further comprising:
evaluating a long-term cardiac activity of said patient based on said EKG data.

9. The method of claim 5, further comprising determining a physical activity level of said patient based on said EKG data.

10. The method of claim 5, further comprising deducing sleep patterns and circadian rhythms of said patient based on said EKG data.

* * * * *